(12) United States Patent
Guryev et al.

(10) Patent No.: US 10,556,216 B2
(45) Date of Patent: Feb. 11, 2020

(54) METHODS AND DEVICES FOR LIPOSOME PREPARATION BY CENTRIFUGATION

(71) Applicant: Becton, Dickinson and Company, Franklin Lakes, NJ (US)

(72) Inventors: Oleg Guryev, San Jose, CA (US); Tatyana Chernenko, San Jose, CA (US); Marybeth Sharkey, San Jose, CA (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 302 days.

(21) Appl. No.: 15/472,053

(22) Filed: Mar. 28, 2017

(65) Prior Publication Data

US 2017/0341049 A1 Nov. 30, 2017

Related U.S. Application Data

(60) Provisional application No. 62/342,112, filed on May 26, 2016.

(51) Int. Cl.
| | |
|---|---|
| *A61K 9/127* | (2006.01) |
| *B01J 13/04* | (2006.01) |
| *B01J 13/12* | (2006.01) |
| *A61K 8/14* | (2006.01) |
| *G01N 33/58* | (2006.01) |

(52) U.S. Cl.
CPC ............... *B01J 13/04* (2013.01); *A61K 8/14* (2013.01); *A61K 9/1271* (2013.01); *A61K 9/1277* (2013.01); *B01J 13/125* (2013.01); *G01N 33/586* (2013.01)

(58) Field of Classification Search
CPC ......... B01J 13/04; G01N 33/586; A61K 8/14; A61K 9/1277
See application file for complete search history.

(56) References Cited

U.S. PATENT DOCUMENTS

| | | | |
|---|---|---|---|
| 4,737,323 A | 4/1988 | Martin et al. | |
| 5,833,860 A | 11/1998 | Kopaciewicz et al. | |
| 6,544,417 B1 | 4/2003 | Tortorella | |
| 6,623,671 B2 | 9/2003 | Coe et al. | |
| 2006/0034907 A1* | 2/2006 | Nagaike | A61K 9/1277 424/450 |

FOREIGN PATENT DOCUMENTS

EP 0460720 B1 8/1996

OTHER PUBLICATIONS

Product description of Microcon® centrifugal filter unit from Sigma Aldrich (https://www.sigmaaldrich.com/catalog/product/sigma/z648051?lang=en&region=US (Year: 2019).*

(Continued)

*Primary Examiner* — Nathan H Empie
(74) *Attorney, Agent, or Firm* — Michael J. Blessent; Bret E. Field; Bozicevic, Field & Francis LLP

(57) ABSTRACT

Methods and devices for producing a population of liposomes are provided. Aspects of the methods include applying a centrifugal force to a suspension of liposomes in a manner sufficient to pass the liposomes through a porous membrane to produce a population of liposomes. Aspects of the invention further include devices, systems and kits useful for performing the methods.

17 Claims, 3 Drawing Sheets

(56) References Cited

OTHER PUBLICATIONS

Kaplan et al ("Poly-N-Acetylglucosamine Matrix Polysaccharaide Impedes Fluid Convection and Transport of the Cationic Surfactant Cetylpyridinium Chloride through Bacterial Biofilms" Applied and Env. Microbio. Mar. 2009, 1308-1314 (Year: 2009).*

Akbarzadeh et al. "Liposome: classification, preparation, and applications," Nanoscale Research Letters, vol. 8, 2013, 102 (9 pages).

Fujii et al. "Liposome display for in vitro selection and evolution of membrane proteins," Nature Protocols, vol. 9, No. 7, 2014, pp. 1578-1591.

Guven et al. "Rapid and efficient method for the size separation of homogeneous fluorescein-encapsulating liposomes," Journal of Liposome Research, vol. 19, No. 2, 2009, pp. 148-154.

Hope et al. "Production of large unilamellar vesicles by a rapid extrusion procedure. Characterization of size distribution, trapped vol. And ability to maintain a membrane potential," Biochimica et Biophysica Acta, vol. 812, 1985, pp. 55-65.

Hope et al. "Chapter 8: Reduction of liposome size and preparation of unilamellar vesicles by extrusion techniques," *Liposome Technology*, $2^{nd}$ Edition. G. Gregoriadis, Ed., CRI Press, Boca Raton, FL, vol. 1, 1993, pp. 124-139.

MacDonald et al. "Small-volume extrusion apparatus for preparation of large, unilamellar vesicles," Biochimica et Biophysica Acta, vol. 1061, 1991, pp. 297-303.

Mayer et al. "Vesicles of variable sizes produced by a rapid extrusion procedure," Biochimica et Biophysica Acta, vol. 858, 1986, pp. 161-168.

Olson et al. "Preparation of liposomes of defined size distribution by extrusion through polycarbonate membranes," Biochimica et Biophysica Acta, vol. 557, 1979, pp. 9-23.

Chen, et al. "Screening of permeable compounds in Flos Lonicerae Japonicae with liposome using ultrafiltration and HPLC", Journal of Pharmaceutical and Biochemical Analysis. Elsevier B.V, Amsterdam, NL, 1-13, vo 1 • 54, No. 2, 2011, pp. 406-419.

Dipali, et al. "Comparative Study of Separation of Non-encapsulated Drug from Unilamellar Liposomes by Various Methods", Journal of Pharmacy and Pharmacology, vol. 48, No. 11, 1996, pp. 1112-111.

Communication pursuant to Rule 164 (1) EPC for European Patent Application No. 17803202.5, dated Oct. 16, 2019, 11 pages.

\* cited by examiner

METHODS AND DEVICES FOR LIPOSOME PREPARATION BY CENTRIFUGATION

CROSS-REFERENCE TO RELATED APPLICATIONS

Pursuant to 35 U.S.C. § 119(e), this application claims priority to the filing date of U.S. Provisional Patent Application Ser. No. 62/342,112, filed May 26, 2016; the disclosures of which applications are incorporated herein by reference.

INTRODUCTION

Liposomes are spherical vesicles that have one or multiple lipid bilayers. Liposomes that include a single lipid bilayer may be referred to as unilamellar liposomes, whereas liposomes that include multiple lipid bilayers may be referred to as multilamellar vesicles. Liposomes can be prepared using different methods, which may depend on factors, such as the lipid composition of the lipid bilayer of the liposomes, the type of medium in which the lipid vesicles are dispersed, the desired size of the liposomes, the desired polydispersity of the liposomes, the robustness and batch-to-batch reproducibility of the production method, and other factors, such as the intended use of the resulting liposomes. For example, liposomes may contain a substance, such as a drug, and be used to deliver the substance to a target area in a patient. Thus, the method used to produce such liposomes may also depend on the physicochemical characteristics of the substance to be entrapped in the liposomes, the concentration of the entrapped substance, or additional processes involved during application/delivery of the liposomes to the patient.

After a suspension of liposomes has been produced, such as a suspension of large, multilamellar vesicles, it may be desirable to produce liposomes having sizes within a certain size range. One common technique for sizing liposomes is sonication, where large, multilamellar vesicles can be disrupted using sonic energy. For example, sonication can be used to produce small, unilamellar vesicles from large, multilamellar vesicles.

SUMMARY

Methods and devices for producing liposomes are provided. Aspects of the methods include applying a centrifugal force to a suspension of liposomes in a manner sufficient to pass the liposomes through a porous membrane to produce a population of liposomes. Aspects of the invention further include devices, systems and kits useful for performing the methods.

DETAILED DESCRIPTION

Figure 1A:
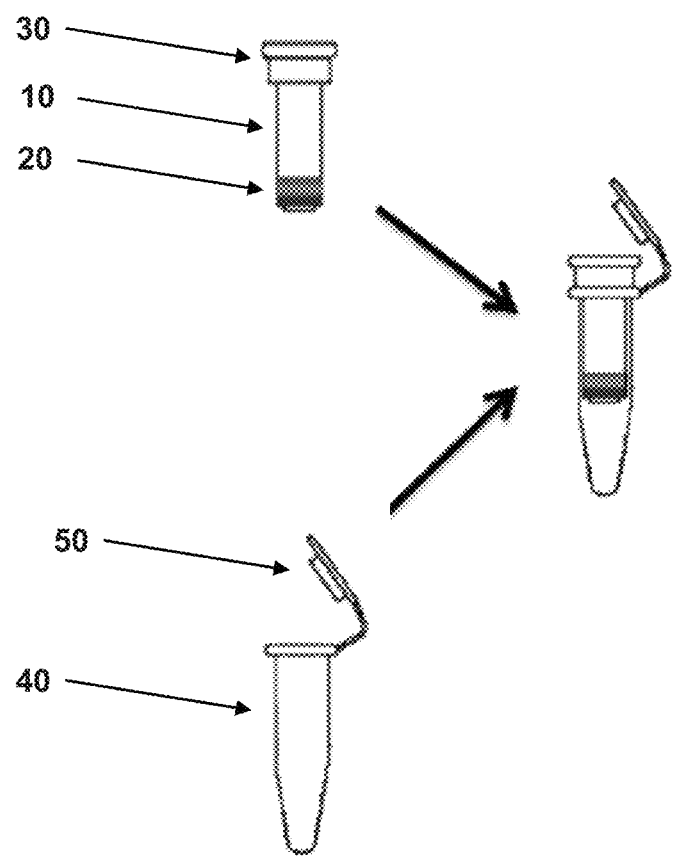
FIG. 1A is an illustration of a liposome extrusion device according to embodiments of the present disclosure.

Methods and devices for producing a population of liposomes are provided. Aspects of the methods include applying a centrifugal force to a suspension of liposomes in a manner sufficient to pass the liposomes through a porous membrane to produce a population of liposomes. Aspects of the invention further include devices, systems and kits useful for performing the methods.

Before embodiments of the present disclosure are described in greater detail, it is to be understood that these embodiments are not limited to the particular embodiments described, as such may vary. It is also to be understood that the terminology used herein is for the purpose of describing particular embodiments only, and is not intended to be limiting, since the scope of the embodiments of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the embodiments of the present disclosure. The upper and lower limits of these smaller ranges may independently be included in the smaller ranges and are also encompassed within the embodiments of the present disclosure, subject to any specifically excluded limit in the stated range. Where the stated range includes one or both of the limits, ranges excluding either or both of those included limits are also included in the embodiments of the present disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the embodiments of the present disclosure, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the embodiments of the present disclosure are not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the embodiments of the present disclosure. Any recited method can be carried out in the order of events recited or in any other order which is logically possible.

As summarized above, the present disclosure provides methods for producing a population of liposomes are provided. In further describing embodiments of the disclosure, the subject methods are first described in greater detail. Next, devices useful for performing the methods are described. In addition, systems, as well as kits that include the subject devices, are also provided.

Methods for Producing Liposomes

Aspects of the present disclosure include methods for producing a population of liposomes. In some instances, the population of liposomes produced by the methods is a population of liposomes of defined size. By defined size is meant that the, because of the manner in which the liposomes are made, the sizes of the various liposomes in the population are known, and specifically the range of liposome sizes in the population is known. In some cases, the liposomes have an average size that is substantially the same. For example, in the case of spherical liposomes, a population of liposomes may have an average diameter that is substantially the same. By "average" is meant the arithmetic mean. Values that are substantially the same include values that vary from each other by 50% or less, such as 45% or less, or 40% or less, or 35% or less, or 30% or less, or 25% or less, or 20% or less, or 15% or less, or 10% or less, or 5% or less, or 3% or less, or 1% or less, or 0.5% or less. In some cases, values that are substantially the same include values that vary from each other by 10% or less. In some cases, values that are substantially the same include values that vary from each other by 5% or less. In some cases, values that are substantially the same include values that vary from each other by 3% or less. In some cases, values that are substantially the same include values that vary from each other by 1% or less. In some cases, values that are substantially the same include values that vary from each other by 0.5% or less. The average size of the liposomes may, in some instances, vary by 50% or less, such as 45% or less, or 40% or less, or 35% or less, or 30% or less, or 25% or less, or 20% or less, or 15% or less, or 10% or less, or 5% or less, or 3% or less, or 1% or less, or 0.5% or less. In some cases, the average size of the liposomes varies by 10% or less. In some cases, the average size of the liposomes varies by 5% or less. In some cases, the average size of the liposomes varies by 3% or less. In some cases, the average size of the liposomes varies by 1% or less. In some cases, the average size of the liposomes varies by 0.5% or less.

In certain embodiments, a population of liposomes may be described by the polydispersity of the liposomes. "Dispersity" or "polydispersity" is a measure of the heterogeneity of sizes of particles in a mixture. In the context of liposomes, polydispersity can range from 0 to 1, where a polydispersity of 0 indicates a monodisperse population of liposomes (e.g., liposomes that have the same average size), and where a polydispersity of 1 indicates a heterogeneous mixture of liposomes. In some cases, the size of liposomes (and thus the polydispersity) can be determined by dynamic light scattering (DLS).

In certain embodiments, methods of the present disclosure are sufficient for producing a population of liposomes from a suspension of liposomes (e.g., an aqueous suspension of liposomes). In some cases, the starting suspension of liposomes includes a population of liposomes having heterogeneous sizes. As such, methods of the present disclosure include starting with a suspension of liposomes (e.g., a population of liposomes having heterogeneous sizes) and producing a population of liposomes from the starting suspension of liposomes.

In some embodiments, the method includes producing a population of liposomes from a suspension of heterogeneous liposomes, where the average size of the population of liposomes varies by 50% or less, such as 45% or less, or 40% or less, or 35% or less, or 30% or less, or 25% or less, or 20% or less, or 15% or less, or 10% or less, or 5% or less, or 3% or less, or 1% or less, or 0.5% or less. In some cases, the method includes producing a population of liposomes from a suspension of heterogeneous liposomes, where the average size of the population of liposomes varies by 10% or less. In some cases, the method includes producing a population of liposomes from a suspension of heterogeneous liposomes, where the average size of the population of liposomes varies by 5% or less. In some cases, the method includes producing a population of liposomes from a suspension of heterogeneous liposomes, where the average size of the population of liposomes varies by 3% or less. In some cases, the method includes producing a population of liposomes from a suspension of heterogeneous liposomes, where the average size of the population of liposomes varies by 1% or less. In some cases, the method includes producing a population of liposomes from a suspension of heterogeneous liposomes, where the average size of the population of liposomes varies by 0.5% or less. In yet other instances, the average size of the disparate liposome members of the population may vary by 50% or more, such as 75% or more, including 100% or more.

In some instances, the starting suspension of liposomes has a higher polydispersity as compared to the produced population of liposomes. Thus, methods of the present disclosure are useful for producing a population of liposomes having a polydispersity less than the polydispersity of the starting suspension of liposomes. In some cases, the polydispersity of the produced population of liposomes is 0.9 or less, such as 0.8 or less, or 0.7 or less, or 0.5 or less, or 0.4 or less, or 0.3 or less, or 0.2 or less, or 0.1 or less, or 0.05 or less, or 0.01 or less. For example, the polydispersity of the produced population of liposomes may be 0.5 or less. In some cases, the polydispersity of the produced population of liposomes may be 0.4 or less. In some cases, the polydispersity of the produced population of liposomes may be 0.3 or less. In some cases, the polydispersity of the produced population of liposomes may be 0.2 or less. In some cases, the polydispersity of the produced population of liposomes may be 0.1 or less. In some cases, the polydispersity of the produced population of liposomes may be 0.05 or less. In some cases, the polydispersity of the produced population of liposomes may be 0.01 or less. In certain instances, the polydispersity of the produced population of liposomes ranges from 0.01 to 0.5, such as 0.01 to 0.4, or 0.01 to 0.3, or 0.01 to 0.2, or 0.01 to 0.1. In other embodiments, the polydispersity of the produced population of liposomes ranges from 0.01 to 0.5, such as 0.01 to 0.5, or 0.01 to 0.4, or 0.01 to 0.3, or 0.01 to 0.2. In other embodiments, the polydispersity of the produced population of liposomes ranges from 0.01 to 0.5, such as 0.05 to 0.5, or 0.1 to 0.5, or 0.1 to 0.4, or 0.1 to 0.3. In other embodiments, the polydispersity of the produced population of liposomes ranges from 0.01 to 0.5, such as 0.05 to 0.5, or 0.1 to 0.5, or 0.2 to 0.5, or 0.2 to 0.4.

In some instances, the starting suspension of liposomes includes liposomes having sizes larger than the produced population of liposomes. In some instances, starting suspension of liposomes includes liposomes having an average size (e.g., an average diameter) of 500 nm or more, such as 600 nm or more, or 700 nm or more, or 800 nm or more, or 900 nm or more, or 1000 nm or more, or 1250 nm or more, or 1500 nm or more, or 1750 nm or more, or 2000 nm or more, or 2250 nm or more, or 2500 nm or more, or 2750 nm or more, or 3000 nm or more, where in some instances the size is 5000 nm or less, such as 4000 nm or less, including 3000 nm or less. For example, the starting suspension of liposomes may include large multilamellar vesicles (LMVs), e.g., multilamellar vesicles having an average size of 200 nm or more, such as ranging from 200 nm to 3,000 nm. In some instances, the starting suspension of liposomes may include large unilamellar vesicles (LUVs), e.g., unilamellar vesicles having an average size of 100 nm or more, such as ranging from 100 nm to 1000 nm.

In some cases, embodiments of the methods may include a step of producing the starting suspension of liposomes. As described above, the suspension of liposomes may be heterogeneous with respect to the sizes of the liposomes in the suspension of liposomes. The suspension of heterogeneous liposomes may be produced using any convenient method for producing liposomes, such as, but not limited to, a solvent dispersion process (e.g., Bangham method, which includes the dissolution of lipids in an organic solvent and then removal of the organic solvent, such as by evaporation of the organic solvent), a detergent removal process (e.g., where detergent-lipid micelles are formed, followed by removal of the detergent to form the liposomes), an injection process (e.g., where lipids are dissolved in an organic solvent and the resulting lipid solution is injected into an aqueous media), a microfluidic process (e.g., where a stream of lipids dissolved in an organic solvent is passed between two aqueous streams in a microfluidic channel), a mechanical dispersion process, a sonication process, combinations thereof, and the like.

Liposomes useful in embodiments of the present disclosure are composed of lipids. In certain embodiments, the lipids are amphiphilic. Amphiphilic lipids may include a hydrophilic group and one or more lipophilic groups covalently bonded to the hydrophilic group. In some cases, the hydrophilic group is a charged group, such as an anionic group or a cationic group. In some instances, the hydrophilic group is an uncharged, polar group. In some embodiments, the hydrophilic group includes a charged group and a polar group. Examples of hydrophilic groups include, but are not limited to, phosphate, phosphocholine, phosphoglycerol, phosphoethanolamine, phosphoserine, phosphoinositol, ethylphosphophorylcholine, polyethyleneglycol, polyglycerol, sphingosine, phosphoshingosine, tri-nitrilotriacetic acid, melamine, glucosamine, trimethylamine, spermine, spermidine, and conjugated carboxylates, sulfates, boric acid, sulfonates, sulfates, carbohydrates, amino acids, and the like. In some cases, the hydrophilic group includes phosphocholine.

In certain embodiments, the lipophilic group includes an aliphatic chain, such as a saturated or unsaturated, linear or branched, substituted or unsubstituted aliphatic chain. For example, the lipophilic group may include an aliphatic chain of 2 to 40 carbon atoms in length, and may be saturated or unsaturated, linear or branched, substituted or unsubstituted. For instance, the lipophilic group may include a saturated or unsaturated, linear or branched, substituted or unsubstituted hydrocarbon chain having from 2 to 40 carbon atoms, such as from 4 to 30 carbon atoms, or from 4 to 25 carbon atoms, or from 6 to 24 carbon atoms, or from 10 to 20 carbon atoms. In certain cases, the lipophilic group includes a saturated or unsaturated, linear or branched hydrocarbon chain having 18 carbon atoms. In certain cases, the lipophilic group includes a saturated or unsaturated, linear or branched hydrocarbon chain having 16 carbon atoms.

Embodiments of the liposomes may include liposomes having a detectable label. In some cases, the detectable label is stably associated with a support. By "stably associated" is meant that a moiety is bound to or otherwise associated with another moiety or structure under standard conditions. Bonds may include covalent bonds and non-covalent interactions, such as, but not limited to, ionic bonds, hydrophobic interactions, hydrogen bonds, van der Waals forces (e.g., London dispersion forces), dipole-dipole interactions, and the like. In certain embodiments, the detectable label is covalently bound to the liposome. For instance, as described above, lipids that comprise the liposome may include a hydrophilic group, which, in some cases may include an activated functional group that provides for a covalent attachment to the detectable label. Any convenient activated functional group useful in chemical synthesis may be used to covalently bond the detectable label to the hydrophilic group of a lipid, such as, but not limited to, amine, carboxyl, amide, hydroxy, azide, maleimide, bromoacetyl, 2-pyridyldithiol, haloalkyl, alkene, or propargyl, or the like.

Liposomes according to embodiments of the present disclosure can include a payload associated with the liposome. As used herein, "payload" refers to a component that is contained within the structure of a liposome, present in a bilayer of a lipid particle, or attached to a surface of a liposome (e.g., by covalent bonds or non-covalent interactions). Thus, a payload can include components that are encapsulated by the liposome (e.g., pharmaceutically active agents, nutriceutical agents, cosmeceutical agents, imaging agents, radiopharmaceutical agents, nuclear magnetic resonance contrast agents, and the like). In certain embodiments, the encapsulated payload is in solution, or may be present as a crystal, as a powder, or a combination thereof. For example, in embodiments where it is desired to provide liposomes with an encapsulated payload (e.g., an encapsulated agent, a therapeutic agent, imaging agent, or the like), such agents may be included in an aqueous phase inside the liposome. Alternatively, in embodiments where the agent is hydrophobic and thus less soluble in water, the hydrophobic agent can be included within a portion of the lipid bilayer.

Embodiments of the methods may also include preparing a liposome extrusion device for use in the method of producing a population of liposomes. Generally, a liposome extrusion device according to embodiments of the present disclosure includes a porous membrane and a component configured to position the membrane in an interior of a liquid container. More detailed aspects of the liposome extrusion device are described in the Devices section below. The component configured to position the membrane in the interior of the liquid container may also be referred to as a membrane component or a membrane support herein. In some instances, the membrane component supports the membrane in the interior of the liquid container. In some cases, the membrane component is removable from the liquid container. As such, embodiments of the method may include positioning the membrane component in the liquid container, and thus positioning the membrane in the liquid container. The membrane component may be positioned in the liquid container prior to introducing a suspension of liposomes into the liposome extrusion device for producing the population of liposomes.

As indicated above, embodiments of the methods include introducing the suspension of liposomes into the liposome extrusion device. The suspension of liposomes may be introduced into the liposome extrusion device such that the suspension of liposomes is positioned on one side of the membrane. For example, the suspension of liposomes may be contained in a chamber on one side of the membrane (e.g., a chamber formed by the membrane component). During production of the population of liposomes, the suspension of liposomes may traverse from one side of the membrane, through the porous membrane, and to the other side of the membrane. For instance, the suspension of liposomes may be contained initially in a first chamber on a first side of the membrane and then, during production of the population of liposomes, may traverse the porous membrane to be contained in a second chamber on the other side of the membrane. In some cases, the second chamber is formed by a portion of the liquid container that contains the membrane component. In certain aspects, the suspension of liposomes is introduced into the liposome extrusion device using any convenient liquid handling technique. For example, a volume of the suspension of liposomes may be added to the liposome extrusion device using any convenient liquid handling apparatus, such as, but not limited to, a syringe, a needle, a pipette, an aspirator, among other liquid handling devices.

Methods of the present disclosure are useful for producing a population of liposomes as described above, e.g., a population of liposomes of defined size. In some embodiments, the population of liposomes has an average size less than the average size of the starting suspension of liposomes. In some cases, the produced population of liposomes has an average size (e.g., an average diameter) of 1000 nm or less, such as 900 nm or less, or 800 nm or less, or 700 nm or less, or 600 nm or less, or 500 nm or less, or 400 nm or less, or 300 nm or less, or 250 nm or less, or 200 nm or less, or 150 nm or less, or 100 nm or less, or 75 nm or less, or 50 nm or less, or 25 nm or less, or 20 nm or less, or 15 nm or less, or 10 nm or less, or 5 nm or less, or 1 nm or less, where in some instances the size average size is 1 nm or more, such as 5 nm or more. In certain instances, the produced population of liposomes has an average size of 1000 nm or less. In certain instances, the produced population of liposomes has an average size of 800 nm or less. In certain instances, the produced population of liposomes has an average size of 500 nm or less. In certain instances, the produced population of liposomes has an average size of 400 nm or less. In certain instances, the produced population of liposomes has an average size of 300 nm or less. In certain instances, the produced population of liposomes has an average size of 250 nm or less. In certain instances, the produced population of liposomes has an average size of 200 nm or less. In certain instances, the produced population of liposomes has an average size of 100 nm or less. In certain instances, the produced population of liposomes has an average size of 50 nm or less. For example, the produced population of liposomes may include small unilamellar vesicles (SUVs), e.g., unilamellar vesicles having an average size of 100 nm or less, such as ranging from 10 nm to 100 nm.

In order to produce the population of liposomes, methods of the present disclosure involve the use of a liposome extrusion device as described herein. As described above, in certain embodiments, the membrane of the liposome extrusion device is a porous membrane and the method includes passing the suspension of liposomes (e.g., a heterogeneous population of liposomes) through the porous membrane to produce a population of liposomes. In certain embodiments, passing the suspension of liposomes through the membrane includes applying a force on the suspension of liposomes such that the liposomes traverse from one side of the membrane to the other side of the membrane. As the liposomes traverse the membrane, the liposomes pass through the pores in the membrane to produce the population of liposomes. The embodiments of the method include extruding a population of liposomes from the porous membrane. In certain instances, the starting suspension of liposomes has an average size that is larger than the pores of the membrane. In some instances, passing larger-sized liposomes through smaller-sized pores in the membrane resizes the liposomes to an average size approximately the same as the size of the pores of the membrane. Thus, in certain cases, passing the liposomes through the membrane produces a population of liposomes.

In some instances, applying a force on the suspension of liposomes includes applying a centrifugal force to the suspension of liposomes in a manner sufficient to pass the liposomes through the membrane to produce a population of liposomes. For example, the method may include the use of a centrifuge, where the suspension of liposomes is placed in the centrifuge and the centrifuge is operated in a manner sufficient to apply a centrifugal force on the suspension of liposomes. The centrifugal force may be applied to the suspension of liposomes such that the liposomes are forced through the pores of the membrane as described above, thus extruding a population of liposomes from the membrane. As such, in some cases, the method includes spinning the suspension of liposomes in a centrifuge. The suspension of liposomes may be contained in a liquid container housing the membrane, and thus the method may include spinning the liquid container containing the suspension of liposomes in a centrifuge such that the liposomes are forced through the pores of the membrane as described above.

In certain embodiments, applying a centrifugal force to the suspension of liposomes includes applying a centrifugal force sufficient to cause the liposomes to pass through the pores of the membrane. In some cases, the applied centrifugal force is greater than standard gravity, such as for example 2 g or more, or 5 g or more, or 10 g or more, or 25 g or more, or 50 g or more, or 100 g or more, or 250 g or more, or 500 g or more, or 750 g or more, or 1000 g or more, or 1500 g or more, or 2000 g or more, or 2500 g or more, or 3000 g or more, or 3500 g or more, or 4000 g or more, or 4500 g or more, or 5000 g or more, or 5500 g or more, or 6000 g or more, or 6500 g or more, or 7000 g or more, or 7500 g or more, or 8000 g or more, or 8500 g or more, or 9000 g or more, or 9500 g or more, or 10,000 g or more.

As described above, in some cases, applying a centrifugal force includes spinning the suspension of liposomes in a centrifuge, and thus in these embodiments, applying a sufficient centrifugal force may include spinning at 10 rpm or more, such as 50 rpm or more, or 100 rpm or more, or 250 rpm or more, or 500 rpm or more, or 750 rpm or more, or 1000 rpm or more, or 1500 rpm or more, or 2000 rpm or more, or 2500 rpm or more, or 3000 rpm or more, or 3500 rpm or more, or 4000 rpm or more, or 4500 rpm or more, or 5000 rpm or more, or 5500 rpm or more, or 6000 rpm or more, or 6500 rpm or more, or 7000 rpm or more, or 7500 rpm or more, or 8000 rpm or more, or 8500 rpm or more, or 9000 rpm or more, or 9500 rpm or more, or 10,000 rpm or more.

In some instances, the centrifugal force is applied for a certain amount of time. The amount of time the centrifugal force is applied may be a time equal to or greater than the time needed for the suspension of liposomes to pass through the pores of the membrane at the applied centrifugal force. For example, the method may include applying a centrifugal force for a time such as 1 min or more, or 2 min or more, or 3 min or more, or 4 min or more, or 5 min or more, or 6 min or more, or 7 min or more, or 8 min or more, or 10 min or more. In some cases, the method may include applying a centrifugal force for a time such as 10 min or less, or 9 min or less, or 8 min or less, or 7 min or less, or 6 min or less, or 5 min or less, or 4 min or less, or 3 min or less, or 2 min or less, or 1 min or less.

In certain embodiments, because a centrifugal force is applied to cause the liposomes to traverse the porous membrane, the methods of the present disclosure may be performed at atmospheric pressure. In some cases, the subject method includes applying the centrifugal force at atmospheric pressure. For example, methods of the present disclosure may not require a pressure greater than atmospheric pressure to be applied to the suspension of liposomes. In some cases, using methods of the present disclosure, a population of liposomes is produced at standard atmospheric pressure. Thus, certain embodiments of the subject methods do not include applying a pressure on the suspension of liposomes, e.g., either manually or by increasing the pressure of a gas or liquid contacting the suspension of liposomes.

As described above, embodiments of the subject method include applying a centrifugal force to the suspension of liposomes in a manner sufficient to pass the liposomes through the membrane to produce a population of liposomes. Some embodiments of the subject methods include applying the centrifugal force to the suspension of liposomes a single time in a manner sufficient to pass the liposomes through the membrane to produce a population of liposomes. In other embodiments, a centrifugal force may be applied more than one time to the suspension of liposomes. For example, the method may include repeating the applying of the centrifugal force to the suspension of liposomes. Thus, applying the centrifugal force may be repeated two or more times. As described above, applying the centrifugal force may result in the suspension of liposomes traversing from one side of the membrane to the other side of the membrane. In some cases, after applying the centrifugal force a first time, the method includes removing the membrane component from the liquid container. Removing the membrane component from the liquid container may allow access to the suspension of liposomes that have traversed the membrane. In some cases, the suspension of liposomes may be collected from the liquid container and the method may be performed on the collected liposomes one or more additional times, e.g., the method may be repeated as described above.

In certain embodiments, the method includes sealing the liposome extrusion device prior to applying the centrifugal force. Sealing the liposome extrusion device may facilitate retention of the suspension of liposomes inside the liposome extrusion device while the centrifugal force is being applied. For example, in some cases, the liquid container includes a seal, such as a cap or a removable cap. Thus, in certain embodiments, the liposome extrusion device is a sealed liposome extrusion device, such as where the liposome extrusion device includes a seal (e.g., a water-tight and/or air-tight seal). In these instances, the method may include removing the seal prior to introducing a volume of the suspension of liposomes into the liposome extrusion device. Removing the seal on the liposome extrusion device may expose the contents of the liposome extrusion device to the surrounding environment and allow access to the interior volume of the liposome extrusion device. Thus, a user that has access to the interior volume of the liposome extrusion device may introduce the volume of the suspension of liposomes into the liposome extrusion device for producing the population of liposomes.

In certain embodiments, the method also includes mixing the contents of the liposome extrusion device after introducing the suspension of liposomes into the liposome extrusion device. The mixing may be performed using any convenient protocol. For example, the mixing may be performed using an agitator. The agitator may be any convenient agitator sufficient for mixing a liquid inside a liquid container, including, but not limited to, vortexers, sonicators, shakers (e.g., manual, mechanical, or electrically powered shakers), rockers, oscillating plates, magnetic stirrers, static mixers, rotators, blenders, mixers, tumblers, orbital shakers, among other agitating protocols.

In some cases, the method also includes assaying the produced population of liposomes. Assaying the population of liposomes may be performed using any suitable assay apparatus. For example, the assay may be for determining the average size of the population of liposomes, the polydispersity of the population of liposomes, or a combination thereof. In some cases, the assay may be performed by dynamic light scattering (DLS). In some cases, the assay apparatus may be a flow cytometer. In these embodiments, the assaying includes flow cytometrically analyzing the population of liposomes. In certain embodiments, the liposomes include a fluorescent label, and thus certain embodiments of the assaying include contacting the population of liposomes with electromagnetic radiation (e.g., light), such as electromagnetic radiation having a wavelength that corresponds to an excitation maxima of the fluorescent label of the liposomes. The assaying may further include detecting emitted light from the excited fluorescent label. For instance, the method may include detecting emitted light from the excited fluorescent label at one or more wavelengths that correspond to the emission maxima of the fluorescent label. In certain embodiments, the population of liposomes may be used in methods for calibrating a flow cytometer, e.g., the population of liposomes may be used as a calibration standard for a flow cytometer.

In certain embodiments, the fluorescent label includes one or more detectable moieties or markers that are detectable based on, for example, fluorescence emission maxima, fluorescence polarization, fluorescence lifetime, light scatter, mass, molecular mass, or combinations thereof. In certain embodiments, the fluorescent label includes a fluorophore (i.e., a fluorescent label, fluorescent dye, etc.). Fluorophores of interest may include but are not limited to dyes suitable for use in analytical applications (e.g., flow cytometry, imaging, etc.). A large number of dyes (e.g., non-polymeric dyes) are commercially available from a variety of sources, such as, for example, Molecular Probes (Eugene, Oreg.) and Exciton (Dayton, Ohio). For example, the fluorophore of the dye may be 4-acetamido-4'-isothiocyanatostilbene-2,2'disulfonic acid; acridine and derivatives such as acridine, acridine orange, acrindine yellow, acridine red, and acridine isothiocyanate; 5-(2'-aminoethyl)aminonaphthalene-1-sulfonic acid (EDANS); 4-amino-N-[3-vinylsulfonyl)phenyl] naphthalimide-3,5 disulfonate (Lucifer Yellow VS); N-(4-anilino-1-naphthyl)maleimide; anthranilamide; Brilliant Yellow; coumarin and derivatives such as coumarin, 7-amino-4-methylcoumarin (AMC, Coumarin 120), 7-amino-4-trifluoromethylcouluarin (Coumaran 151); cyanine and derivatives such as cyanosine, Cy3, Cy3.5, Cy5, Cy5.5, and Cy7; 4',6-diaminidino-2-phenylindole (DAPI); 5', 5"-dibromopyrogallol-sulfonephthalein (Bromopyrogallol Red); 7-diethylamino-3-(4'-isothiocyanatophenyl)-4-methylcoumarin; diethylaminocoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl) aminofluorescein (DTAF), 2'7'-dimethoxy-4'5'-dichloro-6-carboxyfluorescein (JOE), fluorescein isothiocyanate (FITC), fluorescein chlorotriazinyl, naphthofluorescein, and QFITC (XRITC); fluorescamine; IR144; IR1446; Green Fluorescent Protein (GFP); Reef Coral Fluorescent Protein (RCFP); Lissamine™; Lissamine rhodamine, Lucifer yellow; Malachite Green isothiocyanate; 4-methylumbelliferone; ortho cresolphthalein; nitrotyrosine; pararosaniline; Nile Red; Oregon Green; Phenol Red; B-phycoerythrin (PE); o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), 4,7-dichlororhodamine lissamine, rhodamine B sulfonyl chloride, rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, and tetramethyl rhodamine isothiocyanate (TRITC); riboflavin; rosolic acid and terbium chelate derivatives; xanthene; carotenoid-protein complexes, such as peridinin-chlorophyll proteins (PerCP); allophycocyanin (APC); or combinations thereof.

Suitable flow cytometry systems and methods for analyzing samples that may be employed in methods of the invention include, but are not limited to those described in Ormerod (ed.), *Flow Cytometry: A Practical Approach*, Oxford Univ. Press (1997); Jaroszeski et al. (eds.), *Flow Cytometry Protocols*, Methods in Molecular Biology No. 91, Humana Press (1997); *Practical Flow Cytometry*, 3rd ed., Wiley-Liss (1995); Virgo, et al. (2012) *Ann Clin Biochem.* January; 49(pt 1):17–28; Linden, et. al., *Semin Throm Hemost.* 2004 October; 30(5):502–11; Alison, et al. *J Pathol,* 2010 December; 222(4):335–344; and Herbig, et al. (2007) *Crit Rev Ther Drug Carrier Syst.* 24(3):203–255; the disclosures of which are incorporated herein by reference. In certain instances, flow cytometry systems of interest include BD Biosciences FACSCanto™ and FACSCanto II™ flow cytometers, BD Biosciences FACSVantage™, BD Biosciences FACSort™, BD Biosciences FACSCount™, BD Biosciences FACScan™, and BD Biosciences FACSCalibur™ systems, BD Biosciences Influx™ cell sorter, BD Biosciences Accuri™ C6 flow cytometer; BD Biosciences LSR-Fortessa™ flow cytometer, BD Biosciences LSRFortessa™ X-20 flow cytometer, BD Biosciences FACSVerse™ flow cytometer, BD Biosciences FACSAria™ III and BD FACSAria™ Fusion flow cytometers, BD Biosciences FACSJazz™ flow cytometer, or the like. In certain embodiments, the subject systems are flow cytometric systems, such those described in U.S. Pat. Nos. 3,960,449; 4,347,935; 4,667, 830; 5,245,318; 5,464,581; 5,483,469; 5,602,039; 5,643, 796; 5,700,692; 6,372,506 and 6,809,804, the disclosures of which are herein incorporated by reference in their entirety.

Other methods of analysis may also be used, such as, but not limited to, liquid chromatography-mass spectrometry or gas chromatography-mass spectrometry systems. For example, assaying may include the use of an analytical separation device such as a liquid chromatograph (LC), including a high performance liquid chromatograph (HPLC), a micro- or nano-liquid chromatograph or an ultra-high pressure liquid chromatograph (UHPLC) device, a capillary electrophoresis (CE), or a capillary electrophoresis chromatograph (CEC) apparatus. Mass spectrometer (MS) systems may also be used to assay the dye compositions. Examples of mass spectrometers may include, but are not limited to, electrospray ionization (ESI), atmospheric pressure chemical ionization (APCI), electron impact (EI), atmospheric pressure photoionization (APPI), matrix-assisted laser desorption ionization (MALDI) or inductively coupled plasma (ICP) ionization, for example, or any combination thereof. Likewise, any of a variety of different mass analyzers may be employed, including time of flight (TOF), Fourier transform ion cyclotron resonance (FTICR), ion trap, quadrupole or double focusing magnetic electric sector mass analyzers, or any hybrid thereof.

In certain embodiments, the method also includes storing the liposomes for a period of time. The liposomes may be stored for a period of time before and/or after producing the population of liposomes. In some instances, the liposomes are stored for a period of time such as 1 hour or more, or 4 hours or more, or 6 hours or more, or 12 hours or more, or 18 hours or more, or 24 hours or more, or 48 hours or more, or 72 hours or more, or 4 days or more, or 5 days or more, or 6 days or more, or 1 week or more.

Embodiments of the method may further include shipping the liposomes to a remote location. A "remote location," is a location other than the location at which the liposomes are produced. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or one hundred miles or more apart.

Liposome Extrusion Devices

Aspects of the present disclosure include liposome extrusion devices. A liposome extrusion device of the present disclosure is useful for the production of a population of liposomes. Liposome extrusion devices according to certain embodiments of the present disclosure include a porous membrane and a component configured to position the membrane in an interior of a liquid container. Further aspects of each of the elements of the liposome extrusion device are described in more detail below.

As indicated above, the liposome extrusion device includes a porous membrane. A porous membrane is a membrane that includes a plurality of pores in the membrane. The pores may be pores that have defined pore sizes. The size of a pore may be measured as a dimension of the opening of the pore, such as the largest dimension of the opening of the pore. For example, in some cases, the pore is an opening in the membrane having a substantially circular cross section. Thus, in these cases, the pore size can be measured as the diameter of the pore. For instance, the pores in the membrane may have a pore size (e.g., an average pore size) of 1000 nm or less, such as 900 nm or less, or 800 nm or less, or 700 nm or less, or 600 nm or less, or 500 nm or less, or 400 nm or less, or 300 nm or less, or 250 nm or less, or 200 nm or less, or 150 nm or less, or 100 nm or less, or 75 nm or less, or 50 nm or less, or 25 nm or less, or 20 nm or less, or 15 nm or less, or 10 nm or less, or 5 nm or less, or 1 nm or less. In certain instances, the membrane pores have an average pore size of 1000 nm or less. In certain instances, the membrane pores have an average pore size of 800 nm or less. In certain instances, the membrane pores have an average pore size of 500 nm or less. In certain instances, the membrane pores have an average pore size of 400 nm or less. In certain instances, the membrane pores have an average pore size of 300 nm or less. In certain instances, the membrane pores have an average pore size of 250 nm or less. In certain instances, the membrane pores have an average pore size of 200 nm or less. In certain instances, the membrane pores have an average pore size of 100 nm or less. In certain instances, the membrane pores have an average pore size of 50 nm or less. In some embodiments, the pores in the membrane are substantially the same size. Stated another way, the pores in the membrane may be uniform in size. A porous membrane that includes uniformly sized pores may facilitate the production of a population of liposomes.

In certain embodiments, the membrane pores pass through the membrane in a non-tortuous path. For example, the porous membrane may include pores having a longitudinal axis substantially perpendicular to a surface of the membrane. In some cases, the porous membrane may include pores having a longitudinal axis at an angle of less than 90° relative to a surface of the membrane. In certain instances, the porous membrane does not include a web-like or matrix construction where a network of pores are interconnected, thus forming a tortuous path through the membrane. Stated another way, the porous membrane may include distinct pores that pass through the membrane without intersecting other pores in the membrane.

In certain embodiments, the porous membrane is composed of one or more layers of a membrane material. For example, the membrane may be composed of a single layer of a membrane material. In other embodiments, the membrane is composed of two or more layers of a membrane material. For instance, the membrane may include 2 layers of a membrane material, such as 3 or more layers, or 4 or more layers, or 5 or more layers, or 6 or more layers, or 7 or more layers, or 8 or more layers, or 9 or more layers, or 10 or more layers of a membrane material. In some cases, the membrane includes 2 layers of a membrane material. In some cases, the membrane includes 3 layers of a membrane material. In embodiments that include two or more layers of a membrane material, the membrane material of each layer may be the same, or may be different. In certain embodiments, the pore size of each of the two or more layers of the membrane material is the same. In other embodiments, the pore size of at least two of the two or more layers of the membrane material are different.

The membrane may be composed of any suitable membrane material. In some cases, the membrane material is compatible with the liquid and/or liposomes in contact with the membrane. For example, the membrane material can be a liquid-compatible membrane material, such as a hydrophilic membrane material. In some cases, the liposomes may be in an aqueous liquid, and in these cases, the membrane material may be compatible with aqueous media. By "compatible" is meant that the membrane material is substantially inert (e.g., does not significantly react with) the liquid and/or liposomes or other ingredients in contact with the membrane. Examples of suitable membrane materials include polymeric materials, for example, polymers, such as, but not limited to, polycarbonate, polyester, nylon, cellulose, cellulose acetate, polyethylene terephthalate, and the like. In some instances, the membrane material is polycarbonate. In some instances, the membrane material is polyester.

Embodiments if the subject liposome extrusion devices also include a component configured to position the membrane in an interior of a liquid container. The component configured to position the membrane in the interior of the liquid container may also be referred to as a membrane component or a membrane support herein. In some instances, the membrane component supports the membrane in the interior of the liquid container. In addition, the membrane component may be configured to contain a volume of a liquid (e.g., a suspension of liposomes). For instance, the membrane component may include a first end and a second end opposing the first end. In some embodiments, the first end includes an opening. In some instances, the opening in the membrane component exposes the interior of the membrane component to the surrounding environment, e.g., such that the contents of the membrane component are under the same atmospheric pressure as the surrounding environment. For example, the opening may be used for introducing a suspension of liposomes (e.g., a suspension of heterogeneous liposomes) into an interior of the membrane component. In some embodiments, the second end of the membrane component includes a membrane (e.g., a porous membrane as described herein). The membrane component may further include one or more side walls, which form the sides of the membrane component between the opening at the first end of the membrane component and the membrane at the opposing second end of the membrane component. In some instances, there are no gaps between the membrane and the side wall(s) of the membrane component, such that the membrane forms a liquid-tight seal against the side wall(s) of the membrane component. As such, liquid and/or liposomes traversing the membrane may only pass through the pores in the membrane. In certain embodiments, the membrane component is in the shape of a cylinder, where the cylinder has an opening at a first end and the membrane at a second opposing end of the cylinder. In some cases, the membrane component has a circular cross section.

As described above, the membrane component may be configured as a container, where the container is configured to hold a certain volume of a fluid (e.g., gas or liquid). In certain embodiments, the membrane component is configured as a liquid container. For example, the membrane component may be configured to hold a volume of a liquid, such as a suspension of liposomes. The size of the membrane component may depend on the volume of liquid to be held in the membrane component. For instance, the membrane component may be configured to hold a volume (e.g., a volume of a liquid) ranging from 0.1 ml to 1000 ml, such as from 0.1 ml to 900 ml, or 0.1 ml to 800 ml, or 0.1 ml to 700 ml, or 0.1 ml to 600 ml, or 0.1 ml to 500 ml, or 0.1 ml to 400 ml, or 0.1 ml to 300 ml, or 0.1 ml to 200 ml, or 0.1 ml to 100 ml, or 0.1 ml to 50 ml, or 0.1 ml to 25 ml, or 0.1 ml to 10 ml, or 0.1 ml to 5 ml, or 0.1 ml to 2 ml, or 0.1 ml to 1.5 ml, or 0.1 ml to 1 ml, or 0.1 ml to 0.5 ml. In certain instances, the membrane component is configured to hold a volume ranging from 0.1 ml to 5 ml, such as, for example, 0.5 ml, or 1 ml, or 1.5 ml, or 2 ml. In other instances, the membrane component is configured to hold a volume ranging from 0.1 ml to 100 ml, such as 50 ml, or 25 ml.

In certain embodiments, the membrane component has a width (which may also be referred to as the diameter for cylindrical membrane components) ranging from 0.5 cm to 5 cm, such as 0.5 cm to 4.5 cm, or 0.5 cm to 4 cm, or 0.5 cm to 3.5 cm, or 0.5 cm to 3 cm, or 0.5 cm to 2.5 cm, or 0.5 cm to 2 cm, or 0.5 cm to 1.5 cm, or 0.5 cm to 1 cm. In some instances, the membrane component has a width (or diameter) ranging from 0.5 cm to 2.5 cm. In some instances, the membrane component has a width (or diameter) ranging from 0.5 cm to 1 cm. In certain embodiments, the membrane component has a length ranging from 1 cm to 20 cm, such as 1 cm to 15 cm, or 1 cm to 10 cm, or 1 cm to 5 cm, or 1 cm to 2.5 cm. In some instances, the membrane component has a length ranging from 1 cm to 10 cm. In some instances, the membrane component has a length ranging from 1 cm to 5 cm. In some instances, the membrane component has a length ranging from 1 cm to 2.5 cm.

Embodiments of the membrane component can be compatible with the liquid and/or liposomes or other ingredients that may be in contact with the membrane component. Examples of suitable membrane component materials for the liposome extrusion devices include, but are not limited to, plastics, such as polypropylene, polymethylpentene, polytetrafluoroethylene (PTFE), perfluoroethers (PFE), fluorinated ethylene propylene (FEP), perfluoroalkoxy alkanes (PFA), polyethylene terephthalate (PET), polyethylene (PE), polyetheretherketone (PEEK), and the like.

In some cases, the membrane component is configured to position the membrane in an interior of a liquid container. As described above, the membrane component may include a porous membrane at one end of the membrane component. As such, at least a portion of the membrane component may be positioned in the interior of the liquid container such that the membrane of the membrane component is positioned in the interior of the liquid container. In some cases, at least a portion of the membrane component has an outer dimension (e.g., an outer diameter) that is less than an inner dimension (e.g., an inner diameter) of the liquid container. Stated another way, at least a portion of the membrane component, such as the end of the component having the membrane, is sized to fit inside the liquid container. In certain instances, the liquid container has a circular cross section. In these instances, the membrane component may include a cylinder concentric to the interior of the liquid container.

As discussed above, in certain embodiments, the membrane component is configured to position the membrane in an interior of a liquid container. As such, in some instances, the liposome extrusion device includes a liquid container. Embodiments of the subject liquid container may be configured to contain a volume of a liquid (e.g., a suspension of liposomes and/or population of liposomes). In some instances, the liquid container includes a first end and a second end opposing the first end. In some embodiments, the first end includes an opening. In these instances, the opening in the liquid container exposes the interior of the liquid container to the surrounding environment, e.g., such that the contents of the liquid container are under the same atmospheric pressure as the surrounding environment. For example, the opening may be used for positioning the membrane component in the liquid container for production of the population of liposomes. In some cases, at least a portion of the membrane component (e.g., the end of the membrane component having the membrane) is inserted into the liquid container through the opening of the liquid container. In certain instances, the membrane component is removable from the liquid container, such that after applying a centrifugal force in a manner sufficient to pass the liposomes through the membrane, the membrane component may be removed from the liquid container. In these instances, a removable membrane component allows access to the liposomes that have passed through the membrane. These liposomes may be collected and analyzed or re-centrifuged, as described above.

In some instances, the liquid container includes a closed end opposite from the open end of the liquid container. As such, the liquid container may be configured to contain a volume of liquid as described above. The size of the liquid container may depend on the volume of liquid to be held in the liquid container. For instance, the liquid container may be configured to hold a volume (e.g., a volume of a liquid) ranging from 0.1 ml to 1000 ml, such as from 0.1 ml to 900 ml, or 0.1 ml to 800 ml, or 0.1 ml to 700 ml, or 0.1 ml to 600 ml, or 0.1 ml to 500 ml, or 0.1 ml to 400 ml, or 0.1 ml to 300 ml, or 0.1 ml to 200 ml, or 0.1 ml to 100 ml, or 0.1 ml to 50 ml, or 0.1 ml to 25 ml, or 0.1 ml to 10 ml, or 0.1 ml to 5 ml, or 0.1 ml to 2 ml, or 0.1 ml to 1.5 ml, or 0.1 ml to 1 ml, or 0.1 ml to 0.5 ml. In certain instances, the liquid container is configured to hold a volume ranging from 0.1 ml to 5 ml, such as, for example, 0.5 ml, or 1 ml, or 1.5 ml, or 2 ml. In other instances, the liquid container is configured to hold a volume ranging from 0.1 ml to 100 ml, such as 50 ml, or 25 ml.

The liquid container may further include one or more side walls, which form the sides of the liquid container between the opening at the first end of the liquid container and the closed second end of the liquid container. In certain embodiments, the liquid container is in the shape of a cylinder, where the cylinder has an opening at a first end and a closed second opposing end of the cylinder. In some cases, the liquid container has a circular cross section. The shape of the liquid container may vary and may depend on the use of the liposome extrusion device. For example, the liquid container may be configured in a shape that is compatible with the methods of the present disclosure. For instance, the liquid container may be configured in a shape compatible with typical laboratory equipment used to perform the method, such as a shape compatible with a centrifuge. As described above, the liquid container may be configured to hold a volume of a liquid. In these embodiments, the liquid container may be a vial or a test tube. In certain cases, the liquid container is a vial. In certain cases, the liquid container is a test tube. Examples of suitable liquid containers include, but are not limited to, centrifuge tubes, microcentrifuge tubes, Eppendorf® tubes, and the like.

In certain embodiments, the liquid container has a width (which may also be referred to as the diameter for cylindrical liquid containers) ranging from 0.5 cm to 5 cm, such as 0.5 cm to 4.5 cm, or 0.5 cm to 4 cm, or 0.5 cm to 3.5 cm, or 0.5 cm to 3 cm, or 0.5 cm to 2.5 cm, or 0.5 cm to 2 cm, or 0.5 cm to 1.5 cm, or 0.5 cm to 1 cm. In some instances, the liquid container has a width (or diameter) ranging from 0.5 cm to 2.5 cm. In some instances, the liquid container has a width (or diameter) ranging from 0.5 cm to 1 cm. In certain embodiments, the liquid container has a length ranging from 1 cm to 20 cm, such as 1 cm to 15 cm, or 1 cm to 10 cm, or 1 cm to 5 cm, or 1 cm to 2.5 cm. In some instances, the liquid container has a length ranging from 1 cm to 10 cm. In some instances, the liquid container has a length ranging from 1 cm to 5 cm. In some instances, the liquid container has a length ranging from 1 cm to 2.5 cm.

Embodiments of the liquid container can be compatible with the liquid and/or liposomes or other ingredients that may be in contact with the liquid container. Examples of suitable liquid container materials for the liposome extrusion devices include, but are not limited to, plastics, such as polypropylene, polymethylpentene, polytetrafluoroethylene (PTFE), perfluoroethers (PFE), fluorinated ethylene propylene (FEP), perfluoroalkoxy alkanes (PFA), polyethylene terephthalate (PET), polyethylene (PE), polyetheretherketone (PEEK), and the like.

As described above, the membrane component may be configured to position the membrane in an interior of a liquid container when the membrane component (e.g., the end of the membrane component having the membrane) is inserted in the liquid container. In some cases, the membrane component supports the membrane in the interior of the liquid container. The membrane component may support the membrane in the interior of the liquid container such that the end of the membrane component having the membrane is spaced a distance apart from the closed end of the liquid container. In these instances, the liposome extrusion device may be separated into two chambers. The first chamber may be formed by the interior volume of the membrane component. In addition, because the membrane component supports the membrane at a distance apart from the closed end of the liquid container, the volume of space between the membrane of the membrane component and the closed end of the liquid container may form a second chamber. In these embodiments, during use of the liposome extrusion device, a suspension of liposomes (e.g., a heterogeneous suspension of liposomes) may be introduced into the interior volume of the membrane component. Then, applying a centrifugal force to the suspension of liposomes may force the liposomes through the membrane and into the volume of space between the membrane of the membrane component and the closed end of the liquid container (e.g., into the second chamber of the liposome extrusion device).

In certain embodiments, the volume of the liquid container between the end of the membrane component having the membrane and the closed end of the liquid container is equal to or greater than the volume of the membrane component. In these instances, the equal or greater volume of the second chamber of the liposome extrusion device allows may allow the entire volume of the suspension of liposomes in the membrane component to pass through the membrane into the second chamber of the liposome extrusion device. In certain embodiments, when the membrane component is inserted into the liquid container, the distance between the membrane and the closed end of the liquid container ranges from 0.5 cm to 10 cm, such as 0.5 cm to 7 cm, or 0.5 cm to 5 cm, or 0.5 cm to 3 cm, or 0.5 cm to 1 cm. In some instances, the distance between the membrane and the closed end of the liquid container ranges from 0.5 cm to 10 cm. In some instances, the distance between the membrane and the closed end of the liquid container ranges from 0.5 cm to 5 cm. In some instances, the distance between the membrane and the closed end of the liquid container ranges from 0.5 cm to 1 cm. In some instances, when the membrane component is inserted into the liquid container, the volume between the membrane and the closed end of the liquid container ranges from 0.1 ml to 500 ml, such as from 0.1 ml to 400 ml, or 0.1 ml to 300 ml, or 0.1 ml to 200 ml, or 0.1 ml to 100 ml, or 0.1 ml to 75 ml, or 0.1 ml to 50 ml, or 0.1 ml to 25 ml, or 0.1 ml to 10 ml, or 0.1 ml to 5 ml, or 0.1 ml to 2.5 ml, or 0.1 ml to 2 ml, or 0.1 ml to 1.5 ml, or 0.1 ml to 1 ml, or 0.1 ml to 0.5 ml. In certain instances, the volume between the membrane and the closed end of the liquid container ranges from 0.1 ml to 5 ml, such as, for example, 0.5 ml, or 1 ml, or 1.5 ml, or 2 ml. In other instances, the volume between the membrane and the closed end of the liquid container ranges from 0.1 ml to 50 ml, such as 25 ml, or 10 ml.

In some embodiments, as described above, the liquid container is configured as a container, where the container is configured to hold a certain volume of a liquid. In some embodiments, the liquid container may be sealed. That is, the liquid container may include a seal that substantially prevents the contents of the liquid container (e.g., liquid inside the liquid container) from exiting the liquid container. The seal of the liquid container may also substantially prevent other substances from entering the liquid container. For example, the seal may be a water-tight seal that substantially prevents liquids from entering or exiting the liquid container, or may be an air-tight seal that substantially prevents gases from entering or exiting the liquid container.

In some instances, the seal is a removable or breakable seal, such that the contents of the liquid container may be exposed to the surrounding environment when so desired, e.g., if it is desired to remove a portion of the contents of the liquid container. In some instances, the seal is made of a resilient material to provide a barrier (e.g., a water-tight and/or air-tight seal) for retaining the contents of the liquid container inside the liquid container. Particular types of seals include, but are not limited to, films, such as polymer films, caps, etc., depending on the type of container. Suitable materials for the seal include, for example, rubber or polymer seals, such as, but not limited to, silicone rubber, natural rubber, styrene butadiene rubber, ethylene-propylene copolymers, polychloroprene, polyacrylate, polybutadiene, polyurethane, styrene butadiene, and the like, and combinations thereof. For example, in certain embodiments, the seal is a septum pierceable by a needle, syringe, or cannula. The seal may also provide convenient access to a sample in the container, as well as a protective barrier that overlies the opening of the container. In some instances, the seal is a removable seal, such as a threaded or snap-on cap or other suitable sealing element that can be applied to the opening of the liquid container. For instance, a threaded cap can be screwed over the opening before or after a suspension of liposomes has been added to the container. In some cases, the seal is a removable cap, such as a snap-on cap that can be opened before or after a suspension of liposomes has been added to the container. In some embodiments, the seal is attached to the liquid container. In some instances, the seal is configured to provide a closure for the open end of the liquid container. In some instances, the seal is also configured to provide a closure for the open end of the membrane component. Stated another way, both the opening of the liquid container and the opening of the membrane component may be configured to operate with the same type of seal. In these embodiments, the same seal may be used as a closure for the liquid container or the membrane component when the membrane component is inserted into the liquid container.

Certain embodiments of the liposome extrusion device include a porous membrane that includes one or more layers of a polycarbonate material as described herein. The liposome extrusion device may also include a component configured to position the membrane in an interior of a liquid container. The membrane component may have a first end with an opening and a second end opposing the first end. The second end of the membrane component may include the porous membrane.

An example of a liposome extrusion device according to embodiments of the present disclosure is shown in FIG. 1A. In FIG. 1A, the liposome extrusion device is configured as a vial. The liposome extrusion device includes a liquid container 40 in the form of a vial (e.g., an Eppendorf tube) with a cap 50 attached to the liquid container 40. The liposome extrusion device also includes a membrane component 10, which has a first end 30, which has an opening. The open first end 30 of the membrane component exposes the interior volume of the membrane component to the surrounding environment. For instance, the pressure inside the membrane component may be the same as the surrounding atmospheric pressure. The membrane component 10 also includes a porous membrane 20 at a second end of the membrane component 10 opposite the open first end 30. As shown in FIG. 1A, during use, the second end of the membrane component 10 having the membrane 20 may be placed inside the liquid container 40. The membrane component 10 is configured to support the membrane 20 a distance apart from the bottom of the liquid container, thus forming a volume of space between the membrane 20 and the bottom of the liquid container 40. As described herein, the membrane 20 may be composed of one or more layers of a membrane material.

Figure 1B:
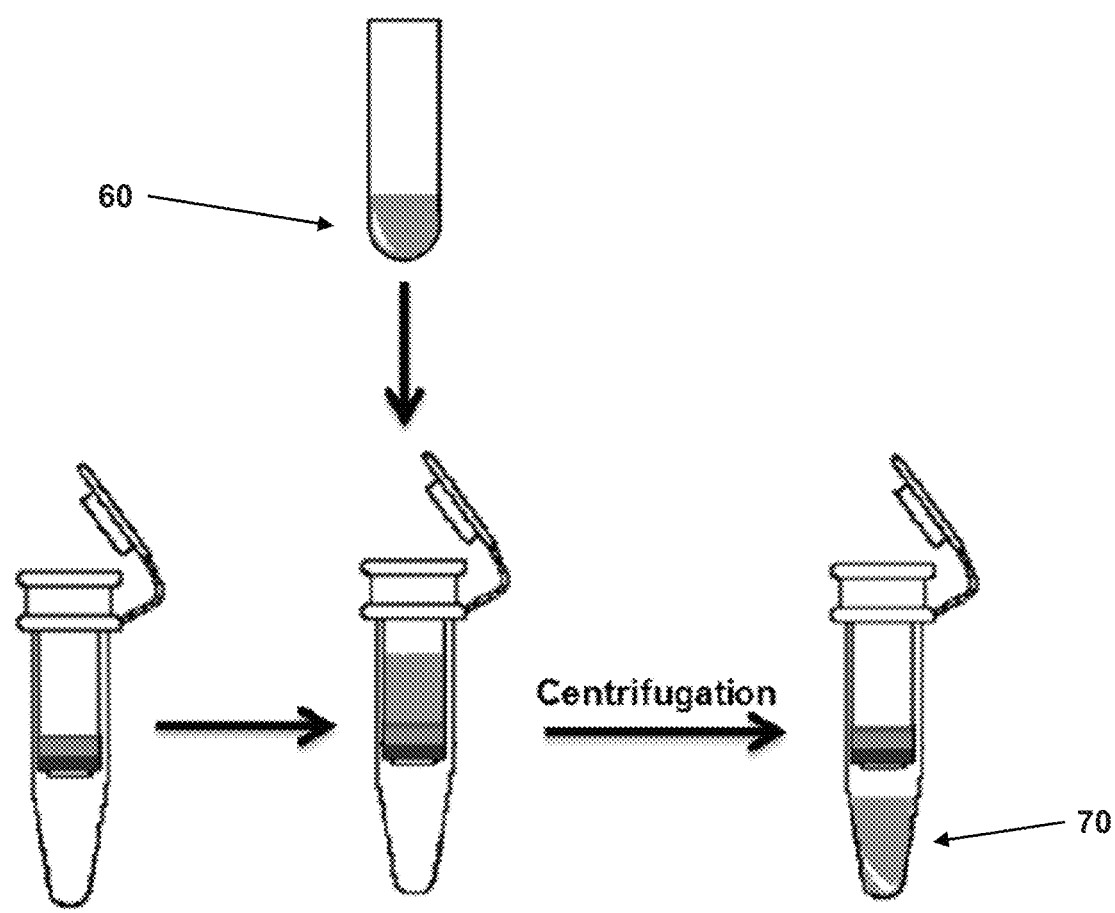
FIG. 1B is an illustration of a methods of using a liposome extrusion device to produce a population of liposomes according to embodiments of the present disclosure.

After the membrane component 10 is positioned in the liquid container 40, a suspension of liposomes 60, such as a heterogeneous suspension of liposomes, can be introduced into the membrane component 10, as shown in FIG. 1B. The cap 50 may be closed (not shown) and the liposome extrusion device may then be placed in a centrifuge. The centrifuge may be operated to apply a centrifugal force to the suspension of liposomes such that the liposomes pass through the porous membrane 20 and into the volume of space between the membrane 20 and the bottom of the liquid container 40. Extrusion of the liposomes through the pores of the membrane may produce a population of liposomes 70, as described herein.

Systems

Systems of the present disclosure include a liposome extrusion device as described herein. For example, the liposome extrusion device may include a porous membrane that includes one or more layers of a polycarbonate material as described herein. The liposome extrusion device may also include a component configured to position the membrane in an interior of a liquid container. The membrane component may have a first end with an opening and a second end opposing the first end. The second end of the membrane component may include the porous membrane. In addition, systems of the present disclosure may also include a liquid container, such as a centrifuge tube, as described herein.

In certain embodiments, the liposome extrusion device includes a suspension of liposomes. For example, during use of the liposome extrusion device, a suspension of heterogeneous liposomes may be introduced into the membrane component. As described herein, a centrifugal force may then be applied to the suspension of liposomes such that the liposomes pass through the porous membrane to produce a population of liposomes. As such, certain embodiments of the systems of the present disclosure may also include a centrifuge. Centrifuges suitable for use in the subject systems include any of the various types of centrifuges. For example, a suitable centrifuge may include a centrifuge configured to apply a centrifugal force to the suspension of liposomes, which may include a centrifuge configured to apply a centrifugal force sufficient to cause the liposomes to pass through the pores of the membrane. In some cases, the centrifuge is configured to apply a centrifugal force greater than standard gravity, such as for example 2 g or more, or 5 g or more, or 10 g or more, or 25 g or more, or 50 g or more, or 100 g or more, or 250 g or more, or 500 g or more, or 750 g or more, or 1000 g or more, or 1500 g or more, or 2000 g or more, or 2500 g or more, or 3000 g or more, or 3500 g or more, or 4000 g or more, or 4500 g or more, or 5000 g or more, or 5500 g or more, or 6000 g or more, or 6500 g or more, or 7000 g or more, or 7500 g or more, or 8000 g or more, or 8500 g or more, or 9000 g or more, or 9500 g or more, or 10,000 g or more, or 15,000 g or more, or 20,000 g or more, or 25,000 g or more, where in some instances the force is 30,000 g or less, such as 27,500 g or less. In some cases, the centrifuge is configured to apply a centrifugal force by spinning at 10 rpm or more, such as 50 rpm or more, or 100 rpm or more, or 250 rpm or more, or 500 rpm or more, or 750 rpm or more, or 1000 rpm or more, or 1500 rpm or more, or 2000 rpm or more, or 2500 rpm or more, or 3000 rpm or more, or 3500 rpm or more, or 4000 rpm or more, or 4500 rpm or more, or 5000 rpm or more, or 5500 rpm or more, or 6000 rpm or more, or 6500 rpm or more, or 7000 rpm or more, or 7500 rpm or more, or 8000 rpm or more, or 8500 rpm or more, or 9000 rpm or more, or 9500 rpm or more, or 10,000 rpm or more.

Kits

Aspects of the disclosure also include kits that include a subject liposome extrusion device. In certain embodiments, the kit includes a subject liposome extrusion device and a packaging configured to hold the liposome extrusion device. The packaging may be a sealed packaging, e.g., a water-resistant and/or water vapor-resistant container, optionally under an air-tight and/or vacuum seal. In certain instances, the packaging is a sterile packaging, configured to maintain the device enclosed in the packaging in a sterile environment. By "sterile" is meant that there are substantially no microbes (such as fungi, bacteria, viruses, spore forms, etc.). In some instances, the kit may also include a liquid container, such as a centrifuge tube, as described herein.

The kits may further include a liquid. For instance, the kit may include a buffer, such as a sample buffer, a wash buffer, an assay buffer, and the like. In some cases, the kit may include a liquid suitable for a suspension of liposomes. The kits may further include additional reagents, such as but not limited to, detectable labels (e.g., fluorescent labels, colorimetric labels, chemiluminescent labels, multicolor reagents, avidin-streptavidin associated detection reagents, radiolabels, gold particles, magnetic labels, etc.), and the like.

In certain embodiments, the kits may also include a calibration standard. For example, the kits may include a set of labelled beads, such as a set of standard fluorescently labelled beads. The calibration standard may be useful for determining the accuracy of the assay apparatus and for ensuring consistency between subsequent assays. For example, the calibration standard may be useful for determining the accuracy of a flow cytometer. In some cases, the calibration standard includes a labelled bead, such as a fluorescently labelled bead. The fluorescently labelled bead may be a standard fluorescently labeled bead that is typically used as a calibration standard. Examples of standard fluorescently labeled beads include, but are not limited to, fluorescently labelled microparticles or nanoparticles. In some cases, the fluorescently labeled beads are configured such that they remain suspended in the assay mixture and do not substantially settle or aggregate. In some embodiments, the fluorescently labeled beads include, but are not limited to, fluorescently labelled polystyrene beads, fluorescein beads, rhodamine beads, and other beads tagged with a fluorescent dye. Additional examples of fluorescently labeled beads are described in U.S. Pat. Nos. 6,350,619; 7,738,094; and 8,248,597, the disclosures of each of which are herein incorporated by reference in their entirety.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Another means would be a computer readable medium, e.g., CD, DVD, Blu-Ray, computer-readable memory (e.g., flash memory), etc., on which the information has been recorded or stored. Yet another form that may be present is a website address which may be used via the Internet to access the information at a removed site. Any convenient form of instructions may be present in the kits.

Utility

The subject methods, devices and systems find use in applications where a population of liposomes of defined size may be desired for research or laboratory testing. In some embodiments, the subject methods, devices and systems facilitate the accurate analysis of analytes (e.g., cells) obtained from a biological sample (e.g., organ, tissue, tissue fragment, fluid). In certain instances, the subject methods, devices and systems find use in testing the accuracy of an apparatus used for the analysis of such analytes for research or laboratory testing. For example, the subject methods, devices and systems find use in testing the accuracy of a flow cytometer. In some cases, the population of liposomes produced using the methods, devices and systems of the present disclosure are used as a calibration standard for an apparatus, such as a flow cytometer. Thus, the subject methods, devices and systems find use in the efficient preparation of a population of liposomes from a suspension of heterogeneous liposomes. In addition, the subject methods, devices and systems find use in the preparation of a population of liposomes without the need for specialized liposome extrusion systems, such as liposome extrusion systems that require syringes or gas/liquid handling components for applying increased pressure on a suspension of liposomes to force the liposomes through an extrusion membrane. In some instances, the subject methods, devices and systems find use in the production of a population of liposomes using standard laboratory equipment at standard atmospheric pressure. Stated another way, the subject methods, devices and systems find use in the production of a population of liposomes without the application of increased pressures on a suspension of liposomes.

As can be appreciated from the disclosure provided above, embodiments of the present disclosure have a wide variety of applications. Accordingly, the examples presented herein are offered for illustration purposes and are not intended to be construed as a limitation on the embodiments of the present disclosure in any way. Those of ordinary skill in the art will readily recognize a variety of noncritical parameters that could be changed or modified to yield essentially similar results. Thus, the following examples are put forth so as to provide those of ordinary skill in the art with a complete disclosure and description of how to make and use embodiments of the present disclosure, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

EXAMPLES

Example 1

Experiments were performed to produce a population of liposomes according to embodiments of the present disclosure.

A dry lipid mixture was prepared by lyophilization or drying under a stream of inert gas, followed by desiccation by vacuum. The dry lipids were hydrated with an aqueous solution (e.g., a buffered saline solution) for 30-60 min. For lipids with a high phase transition temperature, the aqueous solution was pre-warmed before being added to the dry lipids. If desired, the hydrated lipid suspension can be subjected to one or more freeze/thaw cycles, e.g., 3 to 5 freeze/thaw cycles.

A membrane component was placed in a centrifuge tube. For lipids with a high phase transition temperature, the membrane component was pre-warmed. After the dry lipids were hydrated with an aqueous solution, a sample of the aqueous suspension was loaded into the membrane component. The sample was centrifuged. The centrifugation time and speed (rpm) varied depending on the type of membrane used. The centrifugation was repeated if necessary.

A population of liposomes was prepared according to the above procedures using large, multilamellar vesicles (LMVs) composed of 54 mol % 1,2-dioleoyl-sn-glycero-3-phosphocholine (DOPC), 45 mol % cholesterol and 1 mol % N-(fluorescein-5-thiocarbamoyl)-1,2-dihexadecanoyl-sn-glycero-3-phosphoethanolamine, triethylammonium salt (DHPE-F).

An experiment was performed in which the LMVs were centrifuged 3 times in a liposome extrusion device according to the present disclosure that included one polycarbonate membrane having a pore size of 200 nm. The size of the produced population of liposomes, as determined by dynamic light scattering (DLS), was 223.6±0.6 nm.

An experiment was performed in which the LMVs were centrifuged one time in a liposome extrusion device according to the present disclosure that included 3 polycarbonate membranes, each having a pore size of 200 nm. The size of the produced population of liposomes, as determined by DLS, was 210.0±8.2 nm.

An experiment was performed in which the LMVs were centrifuged one time in a liposome extrusion device according to the present disclosure that included 2 polycarbonate membranes, each having a pore size of 400 nm. The size of the produced population of liposomes, as determined by DLS, was 315.6±9.1 nm.

Example 2

Figure 2A:
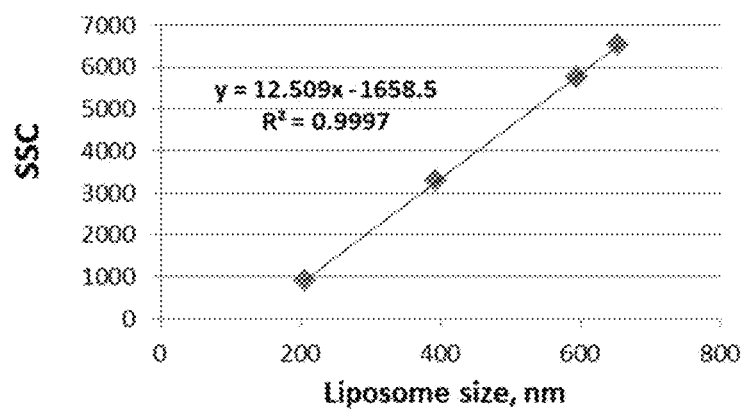
FIGS. 2A and 2B provide data from flow cytometric analysis of liposomes prepared by a centrifugation method of the invention that shows a linear correlation between side scatter (SCC) (FIG. 2A) or fluorescein fluorescence (FIG. 2B) and liposome size.
Figure 2B:
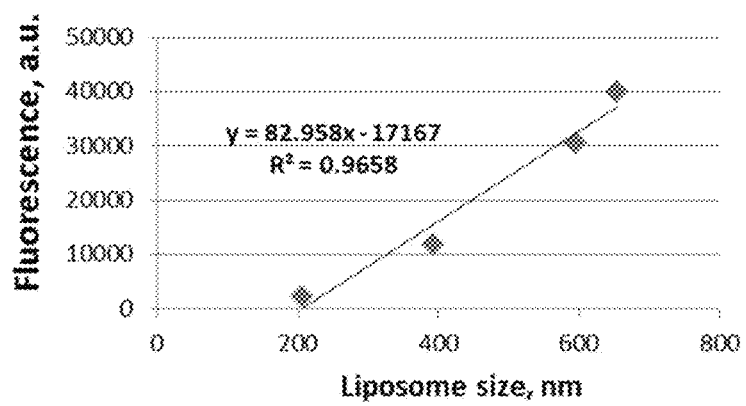

Four populations of liposomes were prepared according to the above procedures using polycarbonate membranes with pore size of 200, 400, 800 or 1000 nm, and LMVs composed of 42 mol % 1-palmitoyl-2-myristoyl-sn-glycero-3-phosphocholine (PMPC), 30 mol % cholesterol, 14 mol % 1,2-dioleoyl-sn-glycero-3-phospho-L-serine (DOPS), 13 mol % 1,2-dioleoyl-sn-glycero-3-phosphoethanolamine (DOPE) and 1 mol % N-(fluorescein-5-thiocarbamoyl)-1,2-dihexadecanoyl-sn-glycero-3-phosphoethanolamine (DHPE-F). Liposome size was analyzed and sized using DLS. BD LSR Fortessa flow cytometer was utilized to analyze side scatter (SSC) and fluorescein fluorescence of the prepared liposomal nanoparticles. The results show a distinct linear correlation between both SSC (FIG. 2, A) or fluorescein fluorescence (FIG. 2, B) and liposome size.

Embodiments

In one embodiment, the present disclosure provides a method for producing a population of liposomes. The method includes introducing a suspension of liposomes into a liposome extrusion device. The liposome extrusion device includes a porous membrane and a component configured to position the membrane in an interior of a liquid container. The method also includes applying a centrifugal force to the suspension of liposomes in a manner sufficient to pass the liposomes through the membrane to produce a population of liposomes.

In some embodiments, the method includes positioning the component in the liquid container prior to introducing the suspension of liposomes into the liposome extrusion device.

In some embodiments, the liquid container is a centrifuge tube.

In some embodiments, the component includes a cylinder concentric to the interior of the liquid container.

In some embodiments, the component includes a first end having an opening, and a second end opposing the first end that includes the membrane. In some embodiments, the second end of the component is spaced a distance apart from a closed end of the liquid container. In some embodiments, a volume of the liquid container between the second end of the component and the closed end of the liquid container is equal to or greater than an interior volume of the component.

In some embodiments, the membrane has a pore size of 1000 nm or less. In some embodiments, the membrane has a pore size of 500 nm or less. In some embodiments, the membrane has a pore size of 250 nm or less.

In some embodiments, the membrane includes one or more layers of a membrane material. In some embodiments, the membrane material is a polymer. In some embodiments, the polymer includes polycarbonate.

In some embodiments, the membrane includes two or more layers of a membrane material. In some embodiments, the pore size of each of the two or more layers of the membrane material is the same. In some embodiments, the pore size of at least two of the two or more layers of the membrane material are different.

In some embodiments, the liquid container includes a seal. In some embodiments, the seal includes a removable cap.

In some embodiments, the applying the centrifugal force includes spinning the liquid container in a centrifuge.

In some embodiments, the applying the centrifugal force is repeated one or more times.

In some embodiments, the applying the centrifugal force is performed at atmospheric pressure.

In some embodiments, the method also includes preparing the suspension of liposomes. In some embodiments, the suspension of liposomes includes a population of liposomes having heterogeneous sizes.

In some embodiments, the liposomes include a fluorescent label.

In some embodiments, the population of liposomes has an average diameter of 1000 nm or less. In some embodiments, the population of liposomes has an average diameter of 500 nm or less. In some embodiments, the population of liposomes has an average diameter of 250 nm or less.

Embodiments of the present disclosure include a liposome extrusion device that includes a porous membrane having one or more layers of a polycarbonate material, and a component configured to position the membrane in an interior of a liquid container and including a first end having an opening, and a second end opposing the first end that includes the membrane.

In some embodiments, the liposome extrusion device also includes the liquid container. In some embodiments, the liquid container is a centrifuge tube.

Embodiments of the present disclosure include a system for producing a population of liposomes. The system includes a liquid container and a liposome extrusion device positioned in the liquid container. The liposome extrusion device includes a porous membrane having one or more layers of a polycarbonate material, and a component configured to position the membrane in an interior of the liquid container and including a first end having an opening, and a second end opposing the first end that includes the membrane.

In some embodiments, the liposome extrusion device contains a suspension of liposomes.

In some embodiments, system also includes a centrifuge.

Embodiments of the present disclosure include a kit. The kit includes a liposome extrusion device and a packaging configured to hold the device. The liposome extrusion device includes a porous membrane having one or more layers of a polycarbonate material, and a component configured to position the membrane in an interior of a liquid container and including a first end having an opening, and a second end opposing the first end that includes the membrane.

In some embodiments, the kit also includes the liquid container.

In some embodiments, the kit includes a set of standard fluorescently labelled beads.

Notwithstanding the appended clauses, the disclosure set forth herein is also defined by the following clauses:

1. A method for producing a population of liposomes, the method comprising:
   introducing a suspension of liposomes into a liposome extrusion device comprising:
   a porous membrane; and
   a component configured to position the membrane in an interior of a liquid container; and
   applying a centrifugal force to the suspension of liposomes in a manner sufficient to pass the liposomes through the membrane to produce a population of liposomes.

2. The method according to Clause 1, further comprising positioning the component in the liquid container prior to introducing the suspension of liposomes into the liposome extrusion device.

3. The method according to Clause 1 or 2, wherein the liquid container comprises a centrifuge tube.

4. The method according to any of Clauses 1 to 3, wherein the component comprises a cylinder concentric to the interior of the liquid container.

5. The method according to any of Clauses 1 to 4, wherein the component comprises a first end having an opening, and a second end opposing the first end and comprising the membrane.

6. The method according to Clause 5, wherein the second end of the component is spaced a distance apart from a closed end of the liquid container.

7. The method according to Clause 6, wherein a volume of the liquid container between the second end of the component and the closed end of the liquid container is equal to or greater than an interior volume of the component.

8. The method according to any of Clauses 1 to 7, wherein the membrane has a pore size of 1000 nm or less.

9. The method according to any of Clauses 1 to 8, wherein the membrane has a pore size of 500 nm or less.

10. The method according to any of Clauses 1 to 9, wherein the membrane has a pore size of 250 nm or less.

11. The method according to any of Clauses 1 to 10, wherein the membrane comprises one or more layers of a membrane material.

12. The method according to Clause 11, wherein the membrane material comprises a polymer.

13. The method according to Clause 12, wherein the polymer comprises polycarbonate.

14. The method according to any of Clauses 11 to 13, wherein the membrane comprises two or more layers of a membrane material.

15. The method according to Clause 14, wherein the pore size of each of the two or more layers of the membrane material is the same.

16. The method according to Clause 14, wherein the pore size of at least two of the two or more layers of the membrane material are different.

17. The method according to any of Clauses 1 to 16, wherein the liquid container comprises a seal.

18. The method according to Clause 17, wherein the seal comprises a removable cap.

19. The method according to any of Clauses 1 to 18, wherein the applying the centrifugal force comprises spinning the liquid container in a centrifuge.

20. The method according to any of Clauses 1 to 19, wherein the applying the centrifugal force is repeated one or more times.

21. The method according to any of Clauses 1 to 20, wherein the applying the centrifugal force is performed at atmospheric pressure.

22. The method according to any of Clauses 1 to 21, further comprising preparing the suspension of liposomes.

23. The method according to any of Clauses 1 to 22, wherein the suspension of liposomes comprises a population of liposomes having heterogeneous sizes.

24. The method according to any of Clauses 1 to 23, wherein the liposomes comprise a fluorescent label.

25. The method according to any of Clauses 1 to 24, wherein the population of liposomes has an average diameter of 1000 nm or less.

26. The method according to any of Clauses 1 to 25, wherein the population of liposomes has an average diameter of 500 nm or less.

27. The method according to any of Clauses 1 to 26, wherein the population of liposomes has an average diameter of 250 nm or less.

28. A liposome extrusion device comprising:
a porous membrane comprising one or more layers of a polycarbonate material; and
a component configured to position the membrane in an interior of a liquid container and comprising a first end having an opening, and a second end opposing the first end and comprising the membrane.

29. The device according to Clause 28, further comprising the liquid container.

30. The device according to Clause 28 or 29, wherein the liquid container comprises a centrifuge tube.

31. The device according to any of Clauses 28 to 30, wherein the component comprises a cylinder concentric to the interior of the liquid container.

32. The device according to Clause 28, wherein the second end of the component is spaced a distance apart from a closed end of the liquid container when the second end of the component is inserted in the liquid container.

33. The device according to Clause 32, wherein a volume of the liquid container between the second end of the component and the closed end of the liquid container is equal to or greater than the volume of the component.

34. The device according to any of Clauses 28 to 33, wherein the membrane has a pore size of 1000 nm or less.

35. The device according to any of Clauses 28 to 34, wherein the membrane has a pore size of 500 nm or less.

36. The device according to any of Clauses 28 to 35, wherein the membrane has a pore size of 250 nm or less.

37. The device according to any of Clauses 28 to 36, wherein the membrane comprises one or more layers of a membrane material.

38. The device according to Clause 37, wherein the membrane comprises two or more layers of a membrane material.

39. The device according to Clause 38, wherein the pore size of each of the two or more layers of the membrane material is the same.

40. The device according to Clause 38, wherein the pore size of at least two of the two or more layers of the membrane material are different.

41. The device according to any of Clauses 28 to 40, wherein the liquid container comprises a seal.

42. The device according to Clause 41, wherein the seal comprises a removable cap.

43. A system for producing a population of liposomes, the system comprising:
a liquid container; and
a liposome extrusion device positioned in the liquid container, wherein the liposome extrusion device comprises:
a porous membrane comprising one or more layers of a polycarbonate material; and
a component configured to position the membrane in an interior of the liquid container and comprising a first end having an opening, and a second end opposing the first end and comprising the membrane.

44. The system according to Clause 43, wherein the liposome extrusion device contains a suspension of liposomes.

45. The system according to Clause 43 or 44, wherein the liquid container comprises a centrifuge tube.

46. The system according to any of Clauses 43 to 45, further comprising a centrifuge.

47. The system according to any of Clauses 43 to 46, wherein the component comprises a cylinder concentric to the interior of the liquid container.

48. The system according to Clause 43, wherein the second end of the component is spaced a distance apart from a closed end of the liquid container when the second end of the component is inserted in the liquid container.

49. The system according to Clause 48, wherein a volume of the liquid container between the second end of the component and the closed end of the liquid container is equal to or greater than the volume of the component.

50. The system according to any of Clauses 43 to 49, wherein the membrane has a pore size of 1000 nm or less.

51. The system according to any of Clauses 43 to 50, wherein the membrane has a pore size of 500 nm or less.

52. The system according to any of Clauses 43 to 51, wherein the membrane has a pore size of 250 nm or less.

53. The system according to any of Clauses 43 to 52, wherein the membrane comprises one or more layers of a membrane material.

54. The system according to Clause 53, wherein the membrane comprises two or more layers of a membrane material.

55. The system according to Clause 54, wherein the pore size of each of the two or more layers of the membrane material is the same.

56. The system according to Clause 54, wherein the pore size of at least two of the two or more layers of the membrane material are different.

57. The system according to any of Clauses 43 to 56, wherein the liquid container comprises a seal.

58. The system according to Clause 57, wherein the seal comprises a removable cap.

59. A kit comprising:
   a liposome extrusion device comprising:
      a porous membrane comprising one or more layers of a polycarbonate material; and
      a component configured to position the membrane in an interior of a liquid container and comprising a first end having an opening, and a second end opposing the first end and comprising the membrane; and a packaging configured to hold the device.

60. The kit according to Clause 59, further comprising the liquid container.

61. The kit according to Clause 59 or 60, wherein the liquid container comprises a centrifuge tube.

62. The kit according to any of Clauses 59 to 61, wherein the component comprises a cylinder concentric to the interior of the liquid container.

63. The kit according to Clause 59, wherein the second end of the component is spaced a distance apart from a closed end of the liquid container when the second end of the component is inserted in the liquid container.

64. The kit according to Clause 63, wherein a volume of the liquid container between the second end of the component and the closed end of the liquid container is equal to or greater than the volume of the component.

65. The kit according to any of Clauses 59 to 64, wherein the membrane has a pore size of 1000 nm or less.

66. The kit according to any of Clauses 59 to 65, wherein the membrane has a pore size of 500 nm or less.

67. The kit according to any of Clauses 59 to 66, wherein the membrane has a pore size of 250 nm or less.

68. The kit according to any of Clauses 59 to 67, wherein the membrane comprises one or more layers of a membrane material.

69. The kit according to Clause 68, wherein the membrane comprises two or more layers of a membrane material.

70. The kit according to Clause 69, wherein the pore size of each of the two or more layers of the membrane material is the same.

71. The kit according to Clause 69, wherein the pore size of at least two of the two or more layers of the membrane material are different.

72. The kit according to any of Clauses 59 to 71, wherein the liquid container comprises a seal.

73. The kit according to Clause 72, wherein the seal comprises a removable cap.

74. The kit according to any of Clauses 59 to 73, further comprising a set of standard fluorescently labelled beads.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of embodiments of the present disclosure. It will be appreciated that those skilled in the art will be able to devise various arrangements which, although not explicitly described or shown herein, embody the principles of embodiments of the present disclosure and are included within its spirit and scope. Furthermore, all examples and conditional language recited herein are principally intended to aid the reader in understanding the principles of embodiments of the present disclosure being without limitation to such specifically recited examples and conditions. Moreover, all statements herein reciting principles, aspects, and embodiments of embodiments of the present disclosure as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the embodiments of the present disclosure, therefore, is not intended to be limited to the exemplary embodiments shown and described herein. Rather, the scope and spirit of embodiments of the present disclosure are embodied by the appended claims.

What is claimed is:

1. A method for producing a population of liposomes, the method comprising:
   introducing a suspension of liposomes into a liposome extrusion device comprising:
      a porous membrane; and
      a component configured to position the membrane in an interior of a liquid container; and
   applying a centrifugal force to the suspension of liposomes in a manner sufficient to pass the liposomes through the membrane to produce a population of liposomes.

2. The method according to claim 1, further comprising positioning the component in the liquid container prior to introducing the suspension of liposomes into the liposome extrusion device.

3. The method according to claim 1, wherein the liquid container comprises a centrifuge tube.

4. The method according to claim 1, wherein the component comprises a cylinder concentric to the interior of the liquid container.

5. The method according to claim 1, wherein the component comprises a first end having an opening, and a second end opposing the first end and comprising the membrane.

6. The method according to claim 5, wherein the second end of the component is spaced a distance apart from a closed end of the liquid container.

7. The method according to claim 6, wherein a volume of the liquid container between the second end of the component and the closed end of the liquid container is equal to or greater than an interior volume of the component.

8. The method according to claim 1, wherein the membrane comprises one or more layers of a membrane material.

9. The method according to claim 8, wherein the membrane material comprises a polymer.

10. The method according to claim 9, wherein the polymer comprises polycarbonate.

11. The method according to claim 1, wherein the liquid container comprises a seal.

12. The method according to claim 1, wherein the applying the centrifugal force comprises spinning the liquid container in a centrifuge.

13. The method according to claim 1, wherein the applying the centrifugal force is repeated one or more times.

14. The method according to claim 1, wherein the applying the centrifugal force is performed at atmospheric pressure.

15. The method according to claim 1, further comprising preparing the suspension of liposomes.

16. The method according to claim 1, wherein the suspension of liposomes comprises a population of liposomes having heterogeneous sizes.

17. The method according to claim 1, wherein the liposomes comprise a fluorescent label.

* * * * *